(12) United States Patent
Caldirola et al.

(10) Patent No.: US 7,582,767 B2
(45) Date of Patent: Sep. 1, 2009

(54) SUBSTITUTED SULPHONAMIDE COMPOUND AND USES THEREOF

(75) Inventors: Patrizia Caldirola, Uppsala (SE); Gary Johansson, Uppsala (SE); Lori Sutin, Danderyd (SE)

(73) Assignee: Biovitrum AB (publ.) (SE)

( * ) Notice: Subject to any disclaimer, the term of this patent is extended or adjusted under 35 U.S.C. 154(b) by 0 days.

(21) Appl. No.: 11/447,524

(22) Filed: Jun. 5, 2006

(65) Prior Publication Data

US 2006/0293361 A1 Dec. 28, 2006

Related U.S. Application Data

(60) Provisional application No. 60/706,523, filed on Aug. 9, 2005.

(30) Foreign Application Priority Data

Jun. 17, 2005 (SE) .................................. 0501383

(51) Int. Cl.
C07D 405/02 (2006.01)
A61K 31/445 (2006.01)
(52) U.S. Cl. ...................... 546/196; 514/320
(58) Field of Classification Search ................. 546/196; 514/320
See application file for complete search history.

(56) References Cited

U.S. PATENT DOCUMENTS

| 3,539,573 | A * | 11/1970 | Fritz et al. ................ 540/551 |
| 7,074,788 | B2 * | 7/2006 | Kurz et al. ............... 514/236.2 |
| 2004/0024210 | A1 * | 2/2004 | Johansson et al. .......... 544/183 |
| 2006/0287291 | A1 * | 12/2006 | Johansson et al. ...... 514/210.19 |

FOREIGN PATENT DOCUMENTS

| WO | WO00/34242 | 6/2000 |
| WO | WO02/100822 | 12/2002 |
| WO | WO04/000828 | 12/2003 |

OTHER PUBLICATIONS

Bentley et al., "5-HT6 Anitsense Oligonucleotide I.C.V. Affects Rat Performance in the Water Maze and Feeding", (abstract) J. of Psychopharm. Suppl. to vol. 11(3): A64:255, 1977.

Bentley et al., "Effect of the 5-HT6 Antagonist, Ro 04-6790 on Food Consumption in Rats Trained to a Fixed Feeding Regime" Br. J. of Pharmacol. Suppl. to vol. 126: p. 66, 1999.

Isaac et al., "6-Bicyclopiperazinyl-1-arylsulfonylindoles and . . . " Bioorg. & Medic. Chem. Letters 10:1719-1721, 2000.

Ruat et al., "A Novel Rat Serotonin (5-HT6) Receptor: Molecular Cloning . . . " Biochem. & Biophys. Res. Comm. 193(1):268-276, 1993.

Sebben et al., "5-HT6 Receptors Positively Coupled to Adenylyl Cyclase in Striatal Neurones in Culture" NeuroReport 5:2553-2557, 1994.

Woolley et al., "A role for 5-HT6 Receptors in Retention of Spatial Learning in the Morris Water Maze" Neuropharmacology 41:210-219, 2001.

* cited by examiner

Primary Examiner—Rita J Desai
Assistant Examiner—John Mabry
(74) Attorney, Agent, or Firm—Fish & Richardson P.C.

(57) ABSTRACT

The present invention relates to compounds of the formula (I),

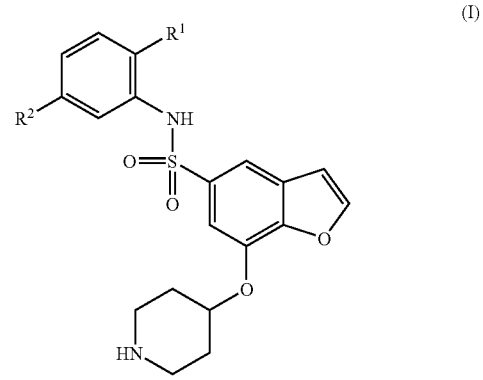

wherein $R^1$ and $R^2$ are as defined in the description; to pharmaceutical formulations comprising these compounds, and to the use of the compounds for the prophylaxis and treatment of medical conditions relating to obesity, type II diabetes, and/or CNS disorders, to achieve reduction of body weight and/or body weight gain.

9 Claims, 2 Drawing Sheets

Fig 1. Effects of 28 days treatment with Example 1 on body weight of DIO rats. Mean ± SEM; n = 10-12. Dunnets t-test P<0.05*, P<0.01, P<0.001* vs vehicle treated controls.

Fig 2. Effects of 28 days treatment with Example 1 on food consumption of DIO rats.
Mean ± SEM; n = 10-12. Dunnets t-test P<0.05*, P<0.01, P<0.001*, Non-significant (ns) vs vehicle treated controls.

SUBSTITUTED SULPHONAMIDE COMPOUND AND USES THEREOF

RELATED APPLICATION INFORMATION

This application claims priority from U.S. provisional application Ser. No. 60/706,523, filed Aug. 9, 2005, and from Swedish application serial no. 0501383-4, filed Jun. 17, 2005, both of which are herein incorporated by reference.

TECHNICAL FIELD

The present invention relates to substituted sulphonamide compounds, to pharmaceutical formulations comprising these compounds, and to the use of the compounds for the prophylaxis and treatment of medical conditions relating to obesity, type II diabetes, and/or disorders of the central nervous system (CNS), to achieve reduction of body weight and/or body weight gain, as well as for cosmetic use.

BACKGROUND ART

Obesity is a condition characterized by an increase in body fat content resulting in excess body weight. Obesity is the most important nutritional disorder in much of the western world and represents a major health problem in all industrialized countries. This disorder leads to increased mortality and decreased well-being due to increased incidences of diseases such as cardiovascular disease, digestive disease, respiratory disease, cancer and type II diabetes. Researchers have long sought compounds that reduce body weight and/or body weight gain. One line of research has been activation of serotoninergic systems, either by direct activation of serotonin receptor subtypes or by inhibiting serotonin reuptake. The exact receptor subtype profile required is however not known.

Serotonin (5-hydroxytryptamine or 5-HT), a key transmitter of the peripheral and central nervous system, modulates a wide range of physiological and pathological functions, including anxiety, sleep regulation, aggression, feeding and depression. Multiple serotonin receptor subtypes have been identified and cloned. One of these, the $5-HT_6$ receptor, was cloned by several groups in 1993 (Ruat, M. et al. (1993) Biochem. Biophys. Res. Commun.193: 268-276; Sebben, M. et al. (1994) NeuroReport 5: 2553-2557). This receptor is positively coupled to adenylyl cyclase and displays affinity for antidepressants such as clozapine. Recently, the effect of $5-HT_6$ antagonist and $5-HT_6$ antisense oligonucleotides to reduce food intake in rats has been reported (Bentley, J. C. et al. (1999) Br J Pharmac. Suppl. 126, P66; Bentley, J. C. et al. (1997) J. Psychopharmacol. Suppl. A64, 255; Woolley M. L. et al. (2001) Neuropharmacology).

Compounds with enhanced affinity and selectivity for the $5-HT_6$ receptor have been identified, e.g. in WO 00/34242 and by Isaac, M. et al. (2000) 6-Bicyclopiperazinyl-1-arylsuifonylindoles and 6-Bicyclopiperidinyl-1-arylsulfonylindoles derivatives as novel, potent and selective $5-HT_6$ receptor antagonists. Bioorganic & Medicinal Chemistry Letters 10: 1719-1721 (2000).

WO 2004/000828 and WO 02/100822, both in the name of Biovitrum AB, disclose sulphonamide derivatives that bind to the $5-HT_6$ receptor and that can be used for the treatment of medical conditions relating to obesity, type II diabetes, and/or CNS disorders.

DISCLOSURE OF THE INVENTION

It has surprisingly been found that the compounds of formula (I) show affinity and selectivity for the $5-HT_6$ receptor as antagonists at low nanomolar range. The affinity and selectivity is unexpectedly high compared to compounds certain compounds in the prior art. Compounds according to the invention and their pharmaceutically acceptable salts have $5-HT_6$ receptor antagonist, agonist and partial agonist activity and are believed to be of potential use in the treatment or prophylaxis of obesity and type II diabetes, to achieve reduction of body weight and/or body weight gain, as well as in the treatment or prophylaxis of disorders of the central nervous system such as anxiety, depression, panic attacks, memory disorders, cognitive disorders, sleep disorders, migraine, anorexia, bulimia, binge disorders, obsessive compulsive disorders, psychoses, Alzheimer's disease, Parkinson's disease, Huntington's chorea and/or schizophrenia, Attention Deficit Hyperactive Disorders (ADHD), drug abuse. The reduction of body weight and/or body weight gain (e.g. treating bodyweight disorders) is achieved inter alia by reduction of food intake. As used herein, the term "body weight disorders" refers to the disorders caused by an imbalance between energy intake and energy expenditure, resulting in abnormal body (e.g., excessive) weight. Such body weight disorders include obesity.

Compounds of Formula (I)

One object of the present invention is a compound of Formula (I):

or a pharmaceutically acceptable salt thereof, wherein:
$R^1$ is methoxy and $R^2$ is methyl; or
$R^1$ is methoxy and $R^2$ is hydroxymethyl; or
$R^1$ is hydroxyl and $R^2$ is methyl.

The compounds of Formula (I) may be used as such or, where appropriate, as pharmacologically acceptable salts (acid or base addition salts) thereof. The pharmacologically acceptable addition salts as mentioned above are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

For clinical use, the compounds of the invention are formulated into pharmaceutical formulations for oral, rectal, parenteral or other mode of administration. Pharmaceutical formulations are usually prepared by mixing the active substance, or a pharmaceutically acceptable salt thereof, with conventional pharmaceutical excipients. The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

Another object of the present invention is a compound above for use in therapy.

Another object of the present invention is a compound above for use in the treatment or prohylaxis of a 5-HT$_6$ receptor related disorder, such as obesity, type II diabetes, and/or CNS disorders, to achieve reduction of body weight and/or body weight gain.

Another object of the present invention is a pharmaceutical formulation comprising a compound above as an active ingredient, in combination with a pharmaceutically acceptable diluent or carrier.

Another object of the present invention is a pharmaceutical formulation comprising a compound above for use in the treatment or prophylaxis of a 5-HT$_6$ receptor related disorder, such as obesity, type II diabetes, and/or disorders of the central nervous system, to achieve reduction of body weight and/or body weight gain.

Another object of the present invention is a method for the treatment or prophylaxis of a 5-HT$_6$ receptor related disorder, such as obesity, type II diabetes, and/or disorders of the central nervous system, to achieve reduction of body weight and/or body weight gain, which comprises administering to a subject in need of such treatment an effective amount of a compound above.

Another object of the present invention is a method for modulating 5-HT$_6$ receptor activity, comprising administering to a subject in need thereof an effective amount of a compound above.

Another object of the present invention is the use of a compound above for the manufacture of a medicament for use in the treatment or prophylaxis of a 5-HT$_6$ receptor related disorder, such as obesity, type II diabetes, and/or disorders of the central nervous system, to achieve reduction of body weight and/or body weight gain.

Examples of disorders of the central nervous system are cognitive disorders including Alzheimer's disease and cognitive impairment associated with schizophrenia.

The methods delineated herein can also include the step of identifying that the subject is in need of treatment of obesity, type II diabetes, or disorders of the central nervous system, or in need of reducing body weight and/or body weight gain.

The invention further relates to cosmetic use of one or more compounds of any of the formulae described herein, for causing loss of weight, as well as cosmetic formulations containing said compounds.

Still further, the invention relates to a non-therapeutic metod for improving the bodily appearance of a mammal, including a human, in which the method comprises orally administering to said mammal one or more compounds of any of the formulae described herein.

"An effective amount" refers to an amount of a compound that confers a therapeutic effect on the treated subject. The therapeutic effect may be objective (i.e., measurable by some test or marker) or subjective (i.e., subject gives an indication of or feels an effect).

For clinical use, the compounds of the invention are formulated into pharmaceutical formulations for oral, rectal, parenteral or other mode of administration. Usually the amount of active compounds is between 0.1-95% by weight of the preparation, preferably between 0.2-20% by weight in preparations for parenteral use and preferably between 1 and 50% by weight in preparations for oral administration.

The typical daily dose of the active substance varies within a wide range and will depend on various factors such as, for example, the individual requirement of each patient and the route of administration. In general, oral and parenteral dosages will be in the range of 50 to 300 mg per day of active substance, preferably 50 to 150 mg per day.

Processes for Preparation

In a further aspect the invention relates to methods of making compounds of any of the formulae herein comprising reacting any one or more of the compounds of the formulae delineated herein, including any processes delineated herein. The compounds of the formulae above may be prepared by, or in analogy with, conventional methods, and especially according to or in analogy with the following methods.

The chemicals used in the above-described synthetic route may include, for example, solvents, reagents, catalysts, protecting group and deprotecting group reagents. The methods described above may also additionally include steps, either before or after the steps described specifically herein, to add or remove suitable protecting groups in order to ultimately allow synthesis of the compounds of any of the formulae described above, their salt forms, or formulations that include the compounds or their salt forms. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

N-[7-(4-piperidinyl)oxy-1-benzofuran-5-yl]-2-methoxy-5-methylbenzenesulfonamide

Example 1 was prepared as follows:

7-iodo-N-(2-methoxy-5-methylphenyl)-1-benzofuran-5-sulfonamide is produced starting from 2,3-dihydrobensofuran. Treatment with chlorosulfonic acid gives the corresponding sulfonyl chloride, which is iodinated using iodine monochloride. Aromatization is done using NBS, resulting in 7-iodo-N-(2-methoxy-5-methylphenyl)-1-benzofuran-5-sulfonamide after treatment with cresidine.

Hydrolysis of 7-iodo-N-(2-methoxy-5-methylphenyl)-1-benzofuran-5-sulfonamide in alkaline solution using copper as catalyst results in 7-hydroxy-N-(2-methoxy-5-methylphenyl)-1-benzofuran-5-sulfonamide. Reaction with a methyl carbamate protected mesylate of 4-hydroxypiperidine, results in methyl 4-[(5-{[(2-methoxy-5-methylphenyl)amino]sulfonyl}-1-benzofuran-7-yl)oxy]piperidine-1-carboxylate, which is hydrolysed in alkaline solution giving the title compound.

EXAMPLE 2

Metabolite of Example 1

N-[7-(4-piperidinyl)oxy-1-benzoftran-5-yl]-5-hydroxymethyl-2-methoxybenzenesulfonamide

EXAMPLE 3

Metabolite of Example 1

N-[7-(4-piperidinyl)oxy-1-benzofuran-5-yl]-2-hydroxy-5-methylbenzenesulfonamide

BIOLOGICAL TESTS

The ability of a compound according to the invention to bind a 5-HT$_6$ receptor, and to be pharmaceutically useful, can be determined using in vivo and in vitro assays known in the art.

(a) 5-HT$_6$ Binding Assay

Binding affinity experiment for the 5-HT$_6$ receptor are performed in HEK293 cells transfected with 5-HT$_6$ receptor using (3H)-LSD as labeled ligand according to the general method as described by Boess F.G et al. Neuropharmacology vol. 36(4/5) 713-720, 1997.

Materials

Cell Culture

The HEK-293 cell line transfected with the 5-HT$_6$ receptor was cultured in Dulbeccos Modified Eagles Medium containing 5% dialyzed foetal bovine serum, (Gibco BRL 10106-169), 0.5 mM sodium pyruvate and 400 µg/ml Geneticin (G-418) (Gibco BRL10131-019). The cells were passaged 1:10, twice a week.

Chemicals

The radioligand [$^3$H] LSD 60-240 Ci/mmol, obtained from Amersham Pharmacia Biotech, (Buckinghamshire, England) was in ethanol and stored at −20° C. The compounds were dissolved in 100% DMSO and diluted with binding buffer.

Disposable

Compounds were diluted in Costar 96 well V-bottom polypropylene plates (Coming Inc. Costar, N.Y., USA). Samples were incubated in Packard Optiplate (Packard Instruments B.V., Groningen, The Netherlands). The total amount of added radioligand was measured in Packard 24-well Barex plates (Packard Instruments B.V., Groningen, The Netherlands) in the presence of Microscint™ 20 scintillation fluid (Packard Bioscience, Meriden, Conn., USA).

Buffer

The binding buffer consisted of 20 mM HEPES, 150 mM NaCl, 10 mM $MgCl_2$, and 1 mM, EDTA, pH 7.4.

Methods

Membrane Preparation

Cells were grown to approximately 90% confluence on 24.5×24.5 NUNC culture dishes. The medium was aspirated, and after rinsing with ice-cold PBS, the cells were scraped off using 25 ml Tris buffer (50 mM Tris-HCl, 1 mM EDTA, 1 mM EGTA, pH 7.4) and a window scraper. The cells were then broken with a Polytron homogeniser, and remaining particulate matter was removed by low-speed centrifugation, 1000×g for 5 min. Finally, the membranes were collected by high-speed centrifugation (20 000×g), suspended in binding buffer, and frozen in aliquots at −70° C.

Radioligand Binding

Frozen cell membranes were thawed, immediately rehomogenized with a Polytron homogenizer, and coupled to SPA wheat germ agglutinin beads (Amersham Life Sciences, Cardiff, England) for 30 min under continuous shaking of the tubes. After coupling, the beads were centrifuged for 10 minutes at 1000 g, and subsequently suspended in 20 ml of binding buffer per 96-well plate The binding reaction was then initiated by adding radioligand and test compounds to the bead-membrane suspension. Following incubation at room temperature, the assay plates were subjected to scintillation counting. The original SPA method was followed except for that membranes were prepared from HEK293 cells expressing the human 5-$HT_6$ receptor instead of from HeLa cells (Dinh D M, Zaworski P G, Gill G S, Schiachter S K, Lawson C F, Smith M W. Validation of human 5-$HT_6$ receptors expressed in HeLa cell membranes: saturation binding studies, pharmacological profiles of standard CNS agents and SPA development. The Upjohn Company Technical Report 7295-95-064 1995; 27 Dec.). The specific binding of [$^3$H] LSD was saturable, while the non-specific binding increased linearly with the concentration of added radioligand. [$^3$H] LSD bound with high affinity to 5-$HT_6$ receptors. The $K_d$ value was estimated to 2.6±0.2 nM based on four separate experiments.

The total binding at 3 nM of [$^3$H] LSD, the radioligand concentration used in the competition experiments, was typically 6000 dpm, and the specific binding more than 70%. 5-HT caused a concentration dependent inhibition of [$^3$H] LSD binding with an over all average Ki value of 236 nM when tested against two different membrane preparations. The inter assay variability over three experiments showed a CV of 10% with an average $K_i$ values of 173 nM (SD 30) and a Hill coefficient of 0.94 (SD 0.09). The intra assay variation was 3% (n=4). Ki values for Example 1 are presented in Table 3. All unlabelled ligands displaced the specific binding of [$^3$H] LSD in a concentration-dependent manner, albeit at different potencies. The rank order of potency for the compounds was methiothepin (2 nM)>mianserin (190 nM)≈5-HT (236 nM)>methysergide (482 nM)>mesulergide (1970 nM).

Protein Determination

Protein concentrations were determined with BioRad Protein Assay (Bradford MM. A rapid and sensitive method for the quantitation of microgram quantities of protein utilizing the principle of protein-dye binding. Anal Biochem 1976;72: 248-54). Bovine serum albumin was used as standard.

Scintillation Counting

The radioactivity was determined in a Packard Top-Count™ scintillation counter (Packard Instruments, Meriden, Conn., USA) at a counting efficiency of approximately 20%. The counting efficiency was determined in separate sets of experiments.

Saturation Experiments

At least 6 concentrations in duplicates of radioligand (0.1-20 nM of [$^3$H] LSD) were used in saturation experiments. The specific binding was calculated as the difference between total binding and non-specific binding, which was determined as the binding of radioligand in the presence of 5 µM lisuride. $B_{max}$ and the dissociation constant, $K_d$, were determined from the non-linear regression analysis using equation 1. $L_u$ is the unbound concentration of radioligand, and is y is the amount bound.

$$y = \frac{B_{max} \cdot Lu}{Lu + Kd} \quad \text{(equation 1)}$$

Competition Experiments

Total-and non-specific binding of radioligand was defined in eight replicates of each. Samples containing test compound were run in duplicate at 11 concentrations. Incubations were carried out at room temperature for 3 hours. The $IC_{50}$ value, i.e. the concentration of test compound that inhibited 50% of the specific binding of radioligand, was determined with non linear regression analysis and the $K_i$ value was calculated using the method of [Cheng Y.C. Biochem. Pharmacol. 22, 3099-3108, 1973S] equation 2.

$$Ki = \frac{IC_{50}}{1 + \frac{L}{K_d}} \quad \text{(equation 2)}$$

L=concentration of radioligand
$K_d$=Affinity of radioligand (b) 5-$HT_6$ Intrinsic Activity Assay Antagonists to the 5-$HT_6$ receptor were characterized by measuring inhibition of 5-HT induced increase in cAMP in HEK 293 cells expressing the human 5-$HT_6$ receptor (see Boess et al. (1997) Neuropharmacology 36: 713-720). Briefly, HEK293/5-$HT_6$ cells were seeded in polylysine coated 96-well plates at a density of 25,000/ well and grown in DMEM (Dulbecco's Modified Eagle Medium) (without phenol-red) containing 5% dialyzed Foetal Bovine Serum for 48 h at 37° C. in a 5% $CO_2$ incubator. The medium was then aspirated and replaced by 0.1 ml assay medium (Hanks Balance Salt Solution containing 20 mM HEPES, 1.5 mM isobutylmethylxanthine and 1 mg/ml bovine serum albumin). After addition of test substances, 50 µl dissolved in assay medium, the cells were incubated for 10 min at 37° C. in a 5% $CO_2$ incubator. The medium was again aspirated and the cAMP content was determined using a radioactive cAMP kit (Amersham Pharmacia Biotech, BIOTRAK RPA559). The potency of antagonists was quantified by determining the concentration that caused 50% inhibition of 5-HT (at [5-HT]=8 times $EC_{50}$) evoked increase in cAMP, using the formula $IC_{50,corr}=IC_{50}/(1+[5HT]/EC_{50})$.

Example 1 has a selective affinity to 5-$HT_6$ receptors with $K_i$ and $IC_{50,corr}$ values between 0.5 nM and 5 µM or display a % inhibition of [$^3$H] LSD≧20% at 50 nM and is an antagonist, agonist or partial agonist at 5-$HT_6$. Example 1 shows good selectivity over 5-$HT_{1a}$, 5-$HT_{2a}$, 5-$HT_{2a}$, 5-$HT_{2b}$, and 5-$HT_{2c}$ (see Table 3 for values).

Additional assays were used for Example 1, see Table 1

TABLE 1

Additional assays used for Example 1

| Assay | Origin | Reference Compound | Bibliography |
|---|---|---|---|
| $\beta_1$ | Human recombinant cells (HEK-293 cells) | Atenolol | Levin et al. (2002) |
| $\beta_2$ | Human recombinant (Sf9 cells) | ICI 118551 | Smith and Teitler (1999) |
| κ (KOP) | Guinea-pig cerebellum | U 50488 | Kinouchi and Pasternak (1991) |
| 5-HT3 | Human recombinant (HEK-293 cells) | MDL 72222 | Hope et al. (1996) |

References in Table 1.

LEVIN, M. C., MARULLO, S., MUNTANER, O., ANDERSON, B. and MAGNUSSON, Y. (2002) The myocardium-protective Gly-49 variant of the beta 1-adrenergic receptor exhibits constitutive activity and increased desensitization and down regulation. *J. Biol. Chem.* 277: 30429-30435

SMITH, C. and TEITLER, M. (1999) Beta-blocker selectivity at cloned human beta$_1$-and beta$_2$-adrenergic receptors. *Cardiovasc. Drugs Ther.*, 13: 123-126.

KINOUCHI, K. and PASTERNAK, G. W. (1991) Evidence for $κ_1$ opioid receptor multiplicity in the guinea pig cerebellum. *Eur. J. Pharmacol.*, 207: 135-141.

HOPE, A. G., PETERS, J. A., BROWN, A. M., LAMBERT, J. J. and BLACKBURN, T. P. (1996) Characterization of a human 5-hydroxytryptamine$_3$ receptor type A (h5-HT$_3$R-A$_s$) subunit stably expressed in HEK 293 cells. *Brit. J. Pharmacol.*, 118: 1237-1245.

(c) Effect on Body Weight and on Food Intake

Materials and Methods

Test Compounds

Example 1 was dissolved in 5% (w/v) PEG 400, 0.2% Tween 80+10 mM sodium acetate buffer, pH 6. The corresponding solution was used as vehicle. The stability of the solutions were checked upon storage for 14 days. Solutions were formulated twice a week and stored in freezer. The solutions were analysed for the actual concentrations and found similar between the two occasions.

Animals

Hundred (100) male Sprague-Dawley rats were raised on high fat diet at Scanbur BK AB (Sollentuna, Sweden) which upon their arrival to the Biovitrum animal care facility weighed approximately 700 g (17 weeks old). The rats were conditioned and weighed for approximately three weeks after their arrival. The rats were singly stored in standard cages during constant room conditions (temp 22+/−1° C., humidity 40-60%, 12 h light/dark cycle, lights off at 10 am). The rats received the same high fat diet (45 kcal % fat, 4.7 kcal/g; D12451) as they received at Scanbur. The diets were purchased from Research Diets, Inc., New Jersey, USA, consisted of pellets and were stored under dry and cold conditions.

Experimental Session

The high fat fed animals which gained the highest weight were selected. This population weighed 799±60 g. The selected forty-eight (48) rats were randomized and divided into five treatment groups in order to obtain as homogeneous groups according to body weight as possible. Each treatment group consisted of 12 rats: Group 1—vehicle, Group 2—Example 1-5 mg/kg (11 μmol/kg), Group 3—Example 1-15 mg/kg (33 μmol/kg), Group 4—Example 1-30 mg/kg (66 μmol/kg). Further nine (9) rats were allocated for measurement of compound exposure and pharmacokinetics at each dose group in parallel for the seventh and the twentyninth days. The study was started by baseline measurements for five days in order to accustom the rats to the procedure and to the experimentalists. Test compound was administered orally once a day at 9-10 am in a volume of 2.5 ml/kg i.e.an average of 2 ml per (800 g) rat. Pellets and body were weighed each day in connection with the injections. Water bottles were weighed once a week. The weighings were done with a computer-assisted Mettler Toledo PR 5002 balance. All data were transferred into an Excel template.

On the twentyeighth day, trunk blood was sampled for determination of serum glucose, insulin, leptin, free fatty acids, triglycerides, cholesterol, HDL, LDL, ALAT, ASAT and urea. Hematocrit was also determined. Epididymal white adipose tissue, liver and gastrocnemius muscle were dissected, and weighed.

Pharmacokinetics

As described above satellite animals for plasma exposure (3 animals/dose) were treated orally with 5, 15 and 30 mg/kg/dag—Example 1. Day 7 blood samples are taken from the tail vein at the time points predose, 10 min. 30 min, 1 h, 2 h, 3 h, 4 h, 6 h, 8 h, och 24 h after dose. From the animals in the treatment group of 15 mg/kg/dag, new blood samples were taken on day 28 at corresponding time points as for day 7. Blood samples (ca 150 μL) were sampled in heparinized tubes and were placed on ice until centrifugation (4000 rpm, 5 min, +4° C.). Plasma was stored at −20° C., until analysis. The blood samples were analysed by HPLC and electrospray ionization tandem mass spectrometry.

Statistics

The food and water intake, and body weight data are calculated in gram and % of basal and expressed as mean +/−SD and/or +/−SEM. The basal value at the day before (day 0) the start of treatment was considered representative since averaging the values over all pretreatment days did not change the results.

The data of body weight and food intake was statistically analysed by two-way univariate ANOVA with repeated measurements (treatment x time) followed by one-way ANOVA for comparison between treatment groups at selected time points. Clinical chemistry measurements were analysed by one-way ANOVA followed by Dunnetts t-test for test of significance of treatment groups versus vehicle control. A difference between two groups was considered significant if P<0.05. Statistical evaluation was performed using SPSS for Windows.

RESULTS

Effect on Body Weight

Figure 1:
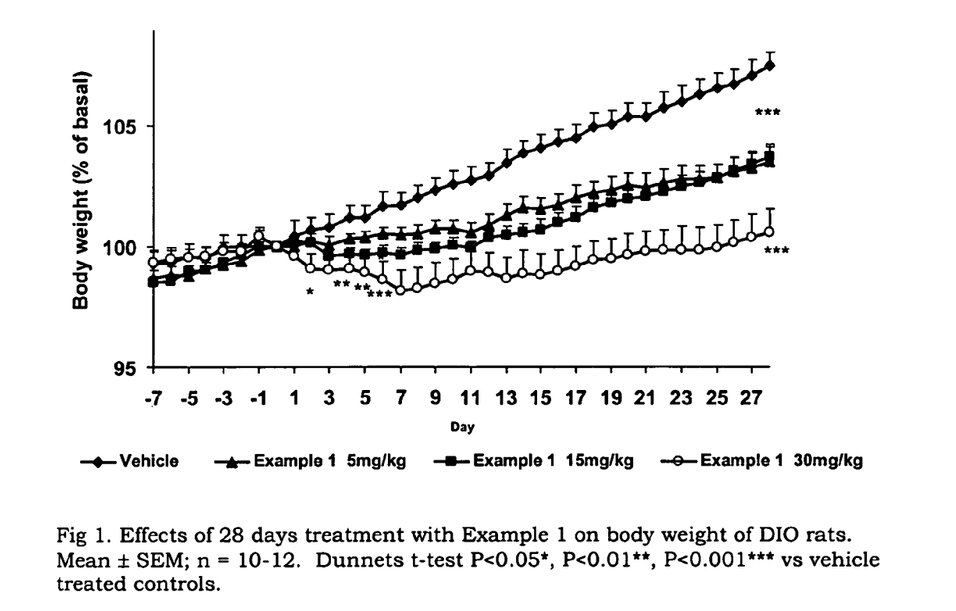
FIG. 1 depicts the results of studies on the effect of the compound of Example 1 on body weight in rats.

The aim of the long-term study was to study whether a prolonged treatment period for four weeks may result in maintained body weight reduction and further be able to determine the minimum effective dose. The doses were selected based on earlier acute and long-term studies with Example 1. The body weight was decreased significantly by Example 1 throughout the whole treatment period (Repeated ANOVA Groups F(3, 42)=12.6; P<0.001) (FIG. 1). The reduction in body weight were 3.9, 3.7 and 6.9% for the doses 5, 15 and 15 mg/kg respectively (Dunnetts t-test P<0.001 for all groups vs vehicle) (See Table 2).

Effect on Food Intake

Figure 2:
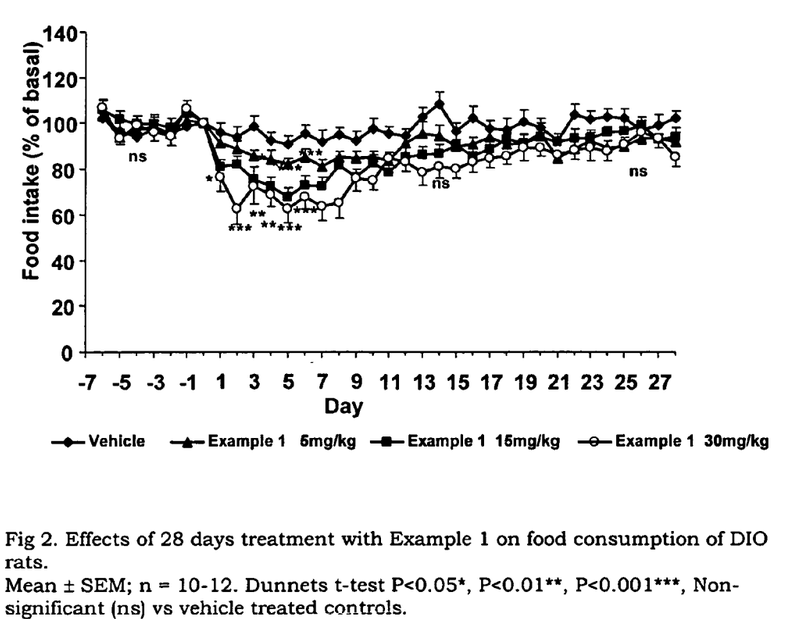
FIG. 2 depicts the results of studies on the effect of the compound of Example 1 on food consumption in rats.

Example 1 decreased food intake significantly during the first seven days as shown in FIG. 2 (Repeated ANOVA Groups F(3, 42)=9.887; P<0.001). Dunnets t-test showed that the doses 15 and 30 mg/kg was significantly different from vehicle (P<0.001) whereas the dose of 5 mg/kg was not. Thus, the minimum effective dose is 15 mg/kg. The effect on food intake attenuated during the days 8 to 14 but remained decreased during the rest of the treatment period, although not statistically significant (Groups F(3, 42)=2.459; P<0.076).

TABLE 4-continued values given for Example 148 (N-(7-piperazin-1-yl-benzofuran-5-yl)-1-naphthylsulphonamide, hydrochloride) in WO 02/100822. For Example 148, the NH-part of the sulphonamide group is bonded to the benzofurane ring.

| Target | Ex. 148 |
|---|---|
| 5-HT2b - Ki | 19.7 nM |
| 5-HT2c - Ki | 158 nM |

TABLE 2

Summary of the effect of 28 days treatment with Example 1 on body weight of DIO rats

| | Single p.o. mg/kg | n | Body weight Mean (g) initial | SD | Body weight Mean (g) Day 28 | SD | Body weight gain Mean (g) | Reduction gram | Basal Mean (%) Day 28 | SD | P | Reduction % of vehicle |
|---|---|---|---|---|---|---|---|---|---|---|---|---|
| Vehicle | | 12 | 807 | 47 | 867 | 42 | 60 | | 107.5 | 2.1 | | |
| Ex. 1 | 5 | 12 | 816 | 76 | 845 | 82 | 29 | −31 | 103.5 | 2.1 | P < 0.001 | 3.9 |
| Ex. 1 | 15 | 12 | 804 | 60 | 834 | 65 | 30 | −30 | 103.7 | 1.9 | P < 0.001 | 3.7 |
| Ex. 1 | 30 | 10 | 806 | 85 | 810 | 76 | 4 | −57 | 100.6 | 3.2 | P < 0.001 | 6.9 |

Body weight gain is calculated as day 28-initial; Reduction means grams or % reduction versus vehicle at day 28.
P values are based on Basal values (%) using Dunnetts t-test.
The mean reduction over days 15 to 28 was 7-12% but only the highest dose reached statistical significance (P < 0.035).

TABLE 3

Biological data for Example 1
In vitro binding at the human 5-HT$_6$ receptor

| Assay | Target | Results |
|---|---|---|
| Binding (Ki) | 5-HT6 | 1.2 nM |
| Functional (inhibition of cAMP activation by 5-HT) (fKi) | 5-HT6 | 2.1 nM |
| Selectivity Binding (Ki) | 5-HT1a | >1000 nM (1400 nM) |
| | 5-HT1b | >1000 nM (3600 nM) |
| | 5-HT2a | >1000 nM (5600 nM) |
| | 5-HT2b | 440 nM |
| | 5-HT2c | >1000 nM (2300 nM) |
| Binding % inihibition 1 μM | β$_1$ | 26, 26 |
| | β$_2$ | 62, 39 |
| | κ (KOP) | 46, 61 (Ki = 120 nM, EC50 = 3780 nM) |
| | 5-HT3 | 61, 71 (Ki 190 nM) |

In Tables 4-6, some values as given in Table 3 for Example 1 are given for a compound disclosed in the prior art:

TABLE 4 values given for Example 148 (N-(7-piperazin-1-yl-benzofuran-5-yl)-1-naphthylsulphonamide, hydrochloride) in WO 02/100822. For Example 148, the NH-part of the sulphonamide group is bonded to the benzofurane ring.

| Target | Ex. 148 |
|---|---|
| 5-HT6 - Ki | 0.18 nM |
| 5-HT6 - fKi | 6 nM |
| 5-HT2a - Ki | 412 nM |

Table 4 shows that Example 1 has a superior selectivity for 5-HT6 to 5-HT2a, 5-HT2b and 5-HT2c compared to Example 148 disclosed in WO 02/100822.

In order to achieve a good selectivity for 5-HT6 to 5-HT2a, 5-HT2b and 5-HT2c, the Ki-binding for the latter receptors is preferably at least 100 fold vs. 5-HT6 binding.

TABLE 5 values given for Compound A (5-chlorothiophene-2-sulphonic acid, [7-(piperidin-4-yloxy)-benzofuran-5-yl]amide, hydrochloride) and Compound B (N-[7-(4-piperidinyloxy)-1-benzofuran-5-yl]-2-trifluoromethylbenzenesulphonamide). For both Compounds A and B, the NH-part of the sulphonamide group is bonded to the benzofurane ring.

| Target | Compound A | Compound B |
|---|---|---|
| 5-HT6 - Ki | 9 nM | 4 nM |
| 5-HT6 - fKi | 6 nM | 3 nM |
| 5-HT1a - Ki | 1515 nM | >1000 nM |
| 5-HT1b - Ki | 1474 nM | 1294 nM |
| 5-HT2a - Ki | >1000 nM | >1000 nM |
| 5-HT2b - Ki | 356 nM | 545 nM |
| 5-HT2c - Ki | >1000 nM | >1000 nM |
| β$_1$ | 80% | 82% |
| β$_2$ | 89% | 82% |
| κ (KOP) | 71% | 83% |
| 5-HT3 | 90% | 91% |

Table 5 shows that Example 1 both has a superior selectivity for 5-HT6 to 5-HT1a, 5-HT1b, 5-HT2a, 5-HT2b and 5-HT2c and superior β1, β2, κ (KOP) and 5-HT3 inhibition values compared to Compounds A and B.

In order to achieve a good selectivity for 5-HT6 to β1, β2, κ (KOP) and 5-HT3, the % inhibition for the latter ones should be ≦70% at 1 μM.

TABLE 6 values given for Compound C (N-[7-(4-piperidinyl)oxy-1-benzofuran-5-yl]-2-methoxy-6-methylbenzenesulphonamide) and Compound D (N-[7-(3-piperidinyl)oxy-1-benzofuran-5-yl]-2-methoxy-5-methylbenzenesulphonamide). For both Compounds C and D, the $SO_2$-part of the sulphonamide group is bonded to the benzofurane ring.

| Target | Compound C | Compound D |
| --- | --- | --- |
| 5-HT6 - Ki | 26 nM | 14 nM |
| 5-HT6 - fKi | 51 nM | 37 nM |
| 5-HT2a - Ki | 1000 nM | 917 nM |
| 5-HT2b - Ki | 600 nM | 1450 nM |
| 5-HT2c - Ki | 1250 nM | 1370 nM |

Table 4 shows that Example 1 has a superior selectivity for 5-HT6 to 5-HT2a, 5-HT2b and 5-HT2c compared to compounds A and B.

What is claimed is:

1. A compound of the formula (I):

(I)

or a pharmaceutically acceptable salt thereof, wherein either:

$R^1$ is methoxy and $R^2$ is methyl; or
$R^1$ is methoxy and $R^2$ is hydroxymethyl; or
$R^1$ is hydroxyl and $R^2$ is methyl.

2. The compound of claim 1, or a pharmaceutically acceptable salt thereof, wherein $R^1$ is methoxy and $R^2$ is methyl.

3. The compound of claim 1, or a pharmaceutically acceptable salt thereof, wherein $R^1$ is methoxy and $R^2$ is hydroxymethyl.

4. The compound of claim 1, or a pharmaceutically acceptable salt thereof, wherein $R^1$ is hydroxyl and $R^2$ is methyl.

5. A pharmaceutical formulation comprising a compound according to claim 1, or a pharmaceutically acceptable salt thereof as an active ingredient, in combination with a pharmaceutically acceptable diluent or carrier.

6. A method for treatment of obesity, comprising administering an effective amount of the compound of claim 1, or a pharmaceutically acceptable salt thereof.

7. A method for treatment of type II diabetes, comprising administering an effective amount of the compound of claim 1, or a pharmaceutically acceptable salt thereof.

8. A method of treating type II diabetes by reducing body weight or reducing body weight gain, comprising administering to a subject in need thereof an effective amount of a compound according to claim 1, or a pharmaceutically acceptable salt thereof.

9. A method for modulating $5\text{-HT}_6$ receptor activity, comprising administering to a subject in need thereof an effective amount of a compound according to claim 1, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 7,582,767 B2 |
| APPLICATION NO. | : 11/447524 |
| DATED | : September 1, 2009 |
| INVENTOR(S) | : Patrizia Caldirola et al. |

It is certified that error appears in the above-identified patent and that said Letters Patent is hereby corrected as shown below:

Title Page, Col. 1, (Other Publications), Line 1, delete "Anitsense" and insert -- Antisense --.

Title Page, Col. 2, (Other Publications), Line 10, delete "Neurones" and insert -- Neurons --.

Signed and Sealed this

Twenty-sixth Day of January, 2010

David J. Kappos
*Director of the United States Patent and Trademark Office*